(12) United States Patent
Kawamuro et al.

(10) Patent No.: US 9,588,072 B2
(45) Date of Patent: Mar. 7, 2017

(54) MEASUREMENT APPARATUS AND METHOD OF MEASUREMENT

(71) Applicant: HIOKI DENKI KABUSHIKI KAISHA, Nagano (JP)

(72) Inventors: Yuki Kawamuro, Nagano (JP); Nobuhisa Handa, Nagano (JP); Tetsuya Takahashi, Nagano (JP)

(73) Assignee: HIOKI DENKI KABUSHIKI KAISHA, Nagano (JP)

( * ) Notice: Subject to any disclaimer, the term of this patent is extended or adjusted under 35 U.S.C. 154(b) by 24 days.

(21) Appl. No.: 14/680,380

(22) Filed: Apr. 7, 2015

(65) Prior Publication Data
US 2015/0293043 A1 Oct. 15, 2015

(30) Foreign Application Priority Data

Apr. 14, 2014 (JP) .................................. 2014-082578
Jun. 27, 2014 (JP) .................................. 2014-131963
Jan. 13, 2015 (JP) .................................. 2015-003797

(51) Int. Cl.
*G01R 31/26* (2014.01)
*C12M 1/00* (2006.01)
*G01N 27/04* (2006.01)

(52) U.S. Cl.
CPC .................................. *G01N 27/04* (2013.01)

(58) Field of Classification Search
CPC ........................................................ G01N 27/04
USPC ............................ 324/439, 693; 204/403.01
See application file for complete search history.

(56) References Cited

U.S. PATENT DOCUMENTS

2007/0105183 A1* 5/2007 Nakatani .......... G01N 33/48728
204/403.01

FOREIGN PATENT DOCUMENTS

JP 2833623 2/1989

* cited by examiner

*Primary Examiner* — Farhana Hoque
(74) *Attorney, Agent, or Firm* — Greenblum & Bernstein, P.L.C.

(57) ABSTRACT

A measurement apparatus includes a measuring unit that carries out a potential measuring process that measures potential at measured positions on a surface of a laminated body, in which a plurality of plate-like or film-like component parts with different physical properties have been laminated, in a state where an electrical signal has been supplied to the surface, and a processing unit that carries out a computational process, which has been decided in advance, using measurement values of the potential that have been measured by the potential measuring process to find an interfacial resistance of an interface between the component parts in the laminated body.

15 Claims, 6 Drawing Sheets

MEASUREMENT APPARATUS AND METHOD OF MEASUREMENT

FIELD OF THE INVENTION

The present invention relates to a measurement apparatus and method of measurement that measure interfacial resistance at interfaces between respective component parts in a laminated body in which a plurality of component parts with respectively different physical properties are laminated.

DESCRIPTION OF THE RELATED ART

Lithium ion cells are known as a construction that uses a laminated body in which a plurality of plate-like or film-like component parts that have respectively different physical properties are laminated. Such a lithium ion cell is fabricated by stacking a plurality of electrodes (laminated bodies in which two film-like component parts are laminated) that are composed of layers of active material formed by applying active material to one or both surfaces of metal foil. Here, one criterion for determining whether each electrode that constructs a lithium ion cell is defective or non-defective is whether the state of adhesion between the metal foil and the active material layer(s) is defective or non-defective. A delamination test (peeling test) and cross-cut adhesion test are known as methods of testing to determine whether such state of adhesion is defective or non-defective. In a delamination test, the extent to which the active material layer is pulled off from the metal foil when adhesive tape that has been stuck onto the surface of the active material layer is lifted off is observed, and the state of adhesion is determined to be defective or non-defective from such observation result. In a cross-cut adhesion test, a plurality of pins that are aligned with a pitch of around 0.5 mm for example are pressed onto the surface of the active material layer of an electrode with a predetermined weight and are moved in a straight line across the surface to scratch the active material layer, the electrode is then rotated by 90°, and the active material layer is scratched with the pins once again in the same way. After this, the extent of delamination of the active material layer produced by such scratching is observed and the state of adhesion is determined to be defective or non-defective from such observation result.

However, in the delamination test and the cross-cut adhesion test described above, since the determination of defective or non-defective is made by observation by the tester, the determination results will be affected by the subjective opinion of the tester, resulting in the problem that it is difficult to accurately make determinations of whether the state of adhesion between a metal foil and an active material layer is defective or non-defective. Since the delamination test and the cross-cut adhesion test also have complicated test procedures and are time-consuming, there is a further problem that the efficiency of testing is poor. By investigating technologies to solve such problems, the present inventors discovered that it is possible to measure the resistance at the interface between metal foil and an active material layer and to determine whether the state of adhesion between the metal foil and the active material layer is defective or non-defective from such measurement and discovered that it would be possible to solve the above problems if the resistance at the interface could be measured easily and accurately. Here, as a technology for measuring the resistance of a plate-like body such as an electrode, a method of measurement that measures resistance (surface resistance and/or volume resistivity) using a four-probe method (for example, the method of measurement disclosed in Japanese Patent No. 2,833,623) is known, and a method that measures interfacial resistance using such method is conceivable.

SUMMARY OF THE INVENTION

However, as a result of investigating the four-probe method mentioned above, the present inventors discovered that it is difficult to accurately measure interfacial resistance between the metal foil and the active material layer that construct the electrode described above using the four-probe method mentioned above. That is, according to the measurement principles, the four-probe method has a premise of measuring resistance of a measured object composed of a single material. This means that when measuring the volume resistivity of a measured object in which a plurality of component parts with respectively different physical properties are laminated, it is difficult to specify whether the measurement is an average of the volume resistivity for the entire measured object or the volume resistivity of a part closest to the surface. Accordingly, it is difficult to accurately measure the resistance of an interface between the metal foil and the active material layer using the four-probe method. In this way, it is difficult, using the conventional four-probe method, to measure the resistance of the interface between the metal foil and the active material layer, which is essential for easily and accurately determining whether the state of adhesion between the metal foil and the active material layer is defective or non-defective, and therefore there is demand for the development of another technology.

The present invention was conceived in view of the problem described above and it is a principal object of the present invention to provide a measurement apparatus and a method of measurement capable of easily and accurately determining whether the state of adhesion of a plurality of component parts in a laminated body, in which a plurality of component parts with respectively different physical properties are laminated, is defective or non-defective.

To achieve the stated object, a measurement apparatus according to the present invention comprises: a measuring unit that carries out a potential measuring process that measures potential at measured positions on a surface of a laminated body, in which a plurality of plate-like or film-like component parts with different physical properties have been laminated, in a state where an electrical signal has been supplied to the surface; and a processing unit that carries out a computational process, which has been decided in advance, using measurement values of the potential that have been measured by the potential measuring process to find an interfacial resistance of an interface between the component parts in the laminated body.

Also, a method of measurement according to the present invention comprises: carrying out a potential measuring process that measures potential at measured positions on a surface of a laminated body, in which a plurality of plate-like or film-like component parts with different physical properties have been laminated, in a state where an electrical signal has been supplied to the surface; and carrying out a computational process, which has been decided in advance, using measurement values of the potential that have been measured by the potential measuring process to find an interfacial resistance of an interface between the component parts in the laminated body.

According to the measurement apparatus and the method of measurement, a potential measuring process that measures the potentials of measured positions on the surface of a laminated body, in which a plurality of component parts with respectively different physical properties are laminated, is carried out, and a computational process which has been decided in advance is carried out using the measured values of potential measured by the potential measuring process to find the interfacial resistance of the interface between the respective component parts in the laminated body. This means that according to the measurement apparatus and the method of measurement, unlike a delamination test or a cross-cut adhesion test that involve complicated tasks, it is possible to accurately and easily determine whether the state of adhesion between component parts is defective or non-defective based on the interfacial resistance that has been measured. Also, according to the measurement apparatus and the method of measurement, by measuring the resistance according to completely different measurement principles to the four-probe method that has a premise of measuring resistance of an object to be measured which is formed of a single material, it is possible to accurately measure the resistance at the interface in a laminated body in which a plurality of component parts with respectively different physical properties have been laminated. Accordingly, according to the measurement apparatus and the method of measurement, for example, it is possible to accurately and easily determine whether the state of adhesion between the metal foil and the active material layer of a lithium ion cell, which is constructed by laminating the metal foil and the active material layer that have different physical properties, is defective or non-defective.

Also, in the measurement apparatus according to the present invention, the processing unit carries out, as the computational process, a process that plugs a plug resistance as a plug value of the interfacial resistance into an equation that has the interfacial resistance as a parameter to calculate computed values of potential and carries out a comparison process that compares the computed values with the measured values while changing the plug resistance and sets, as the interfacial resistance, the plug resistance when a comparison result of the comparison process satisfies a predefined condition that is defined in advance.

Also, in the method of measurement according to the present invention, a plug resistance as a plug value of the interfacial resistance is plugged into an equation that has the interfacial resistance as a parameter to calculate computed values of potential and a comparison process that compares the computed values with the measured values measured by the potential measuring process is carried out while changing the plug resistance, and a process that sets the plug resistance when a comparison result of the comparison process satisfies a predefined condition that is defined in advance as the interfacial resistance is carried out as the computational process.

By using such construction, it is possible to make arbitrary adjustments in accordance with the object of finding the interfacial resistance, such as strictly defining the predefined condition to raise the precision of the interfacial resistance or relaxing the predefined condition to reduce the processing time with priority over improvement of the precision of the interfacial resistance.

Also, in the measurement apparatus according to the present invention, the processing unit plugs the plug resistance and plug resistivities as plug values for resistivities of the component parts into the equation that includes the interfacial resistance and the resistivities of the component parts as parameters to calculate the computed values and carries out the comparison process that compares the computed values with the measured values while changing the plug resistance and the plug resistivities, and sets the plug resistance when the comparison result of the comparison process satisfies the predefined condition as the interfacial resistance and sets the plug resistivities when the comparison result of the comparison process satisfies the predefined condition as the resistivities.

By using such construction, when a resistivity of component parts is unknown, it is possible to measure such resistivity together with the interfacial resistance. Accordingly, according to the measurement apparatus, in addition to it being possible to accurately and easily determine whether the state of adhesion between the component parts of the laminated body is defective or non-defective, it is also possible to accurately and easily determine whether the component parts have the prescribed physical properties, for example, and as a result it is possible to make a detailed determination of whether the laminated body is defective or non-defective.

Also, in the measurement apparatus according to the present invention, in the potential measuring process, the measuring unit measures, in a state where the electrical signal has been supplied to two signal input positions on the surface of a component part, the potential at at least three measured positions that are positions inside a partitioned area on the surface that is partitioned between two straight lines that pass the signal input positions and are perpendicular to a line that joins the signal input positions, the positions having different separation distances from one of the signal input positions, and the processing unit calculates a difference in the measured values at a pair of measured positions out of the measured positions for a plurality of different combinations in the pair of measured positions, calculates, based on a relational expression defining a relationship between a first ratio that is a ratio between the differences for the plurality of combinations and a second ratio that is a ratio between the resistance of the composite body specified from the resistivity and the interfacial resistance, respective initial values of the plug resistance and the plug resistivity to be initially plugged into the equation in the comparison process, and carries out the comparison process.

By using such construction, by using the initial values of the plug resistance and the plug resistivity calculated by the calculating method described above, it is possible to produce a state where the initial comparison result of the comparison process and the predefined condition are quite close. This means that according to this measurement apparatus, compared to a configuration that arbitrarily define the initial values of the plug resistance and the plug resistivity, it is possible to reduce the number of iterations of various processes until the comparison result satisfies the predefined condition. Accordingly, according to the present measurement apparatus, it is possible to sufficiently reduce the time required to measure the interfacial resistance.

Also, in the measurement apparatus according to the present invention, the measuring unit measures, in a state where the electrical signal has been supplied to two signal input positions on the surface of a composite body that has a high resistivity out of the composite bodies in the laminated body in which two composite bodies with respectively different resistivities have been laminated, the potential at three measured positions with respectively different separation distances from the one of the signal input positions, and the processing unit calculates the initial values based on the relational expression that defines the relationship between the first ratio and the second ratio for two pairs as the plurality of different combinations.

By using such construction, compared to a configuration that measures the potential at three or more measured positions and calculate the initial values of the plug resistance and the plug resistivity based on a relational expression that defines the relationship between the first ratio and the second ratio for three or more pairs, the calculation of the initial values is simplified, which makes it possible to further reduce the time required to measure the interfacial resistance.

Also, in the measurement apparatus according to the present invention, the processing unit sets a measured position with a shortest separation distance from the one of the signal input positions as a reference position and calculates the initial values with the reference position as one of the measured positions in the two pairs.

By using such construction, compared to a configuration that calculates the respective initial values using the difference found with adjacent measured positions as the pairs, since the differences of the respective pairs are clearly different, it is possible to set the initial values of the plug resistance and the plug resistivity calculated by plugging such differences into the relational expression at more appropriate values.

Also, in the measurement apparatus according to the present invention, the processing unit sets a first measured position, out of two measured positions aside from the reference position, at a short separation distance from the reference position and the reference position as a first pair, sets a second measured position, out of the two measured positions, at a long separation distance from the reference position and the reference position as a second pair, and calculates the initial values based on the relational expression that has a ratio of the differences for the first pair to a ratio of the differences for the second pair as the first ratio and has a ratio of the resistance of the component part to the interfacial resistance as the second ratio.

By using such construction, by defining and standardizing the measured positions that compose the respective pairs in this way, it is possible, when generating the relational expression between the first ratio and the second ratio, to standardize appropriate coefficients that associate the first ratio and the second ratio, by doing so it becomes easy to generate the relational expression, and as a result it is possible to calculate the initial values of the plug resistance and the plug resistivity much more easily.

Also, in the measurement apparatus according to the present invention, the measured positions are set on a line that joins the signal input positions.

By using such construction, a change in potential in accordance with the separation distance from the signal input position will clearly appear compared to a configuration where the measured positions are not located on a single straight line, for example. This means that according to the present measurement apparatus, it is possible to set the initial values of the plug resistance and the plug resistivity calculated by plugging the differences found from the potentials into the relational expression that defines the relationship between the first ratio and the second ratio at more appropriate values.

Also, in the measurement apparatus according to the present invention, the second measured position is set at a center of the line.

By using such construction, the potential at each position on the line will normally have the same magnitude but with opposite polarity, centered on the center of the line. This means, since it is possible to define the first ratio using the difference between the potential of a measured position set between one of the signal input positions and the center of the line, it is possible to simplify the relational expression that defines the relationship between the first ratio and the second ratio, and as a result it is possible to greatly simplify the calculation of the initial values of the plug resistance and the plug resistivity.

Also, in the measurement apparatus according to the present invention, the measured positions are set so that intervals between adjacent measured positions are equal.

By using such construction, compared to a measurement apparatus where the intervals between adjacent measured positions are different, it is possible to simplify the relational expression that defines the relationship between the first ratio and the second ratio, and therefore possible to calculate the initial values of the plug resistance and the plug resistivity even more easily.

Also, in the measurement apparatus according to the present invention, the processing unit carries out, as the comparison process, a process that calculates differences between the measured values and the computed values as the comparison result and determines that the predefined condition is satisfied when a value calculated by a statistical method using the differences is below a predefined value that has been defined in advance.

By using such construction, when for example the number of measured positions is 2 or higher, by using least sum of squares as the statistical method, it is possible to sufficiently improve the measurement precision of the interfacial resistance and the resistivities. As a result, it is possible to accurately determine whether the state of adhesion between the component parts of the laminated body is defective or non-defective and also possible to accurately determine whether the component parts have the prescribed physical properties.

It should be noted that the disclosure of the present invention relates to the contents of Japanese Patent Application 2014-82578 that was filed on 14 Apr. 2014, Japanese Patent Application 2014-131963 that was filed on 27 Jun. 2014, Japanese Patent Application 2015-3797 that was filed on 13 Jan. 2015, and the entire contents of which are herein incorporated by reference.

BRIEF DESCRIPTION OF THE DRAWINGS

These and other objects and features of the present invention will be explained in more detail below with reference to the attached drawings, wherein.

DESCRIPTION OF THE PREFERRED EMBODIMENTS

Preferred embodiments of a measurement apparatus and method of measurement according to the present invention will now be described with reference to the attached drawings.

First, the configuration of a measurement apparatus 1 shown in FIG. 1 as an example of a measurement apparatus will be described. As one example, the measurement apparatus 1 is configured so as to be capable of measuring the interfacial resistance at the interfaces between component parts that construct a positive electrode 100a and a negative electrode 100b (both of which correspond to "laminated bodies") of a lithium ion cell 200 shown in FIG. 2 and also the resistivities of the respective component parts.

Figure 2:
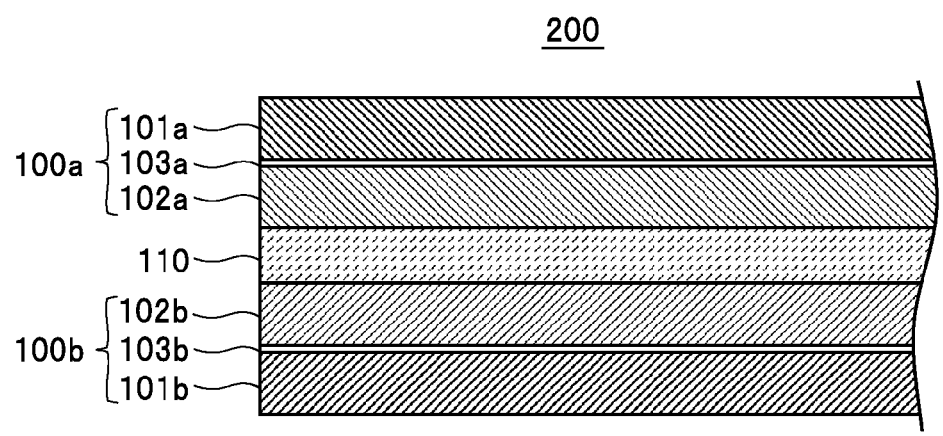
FIG. 2 is a schematic diagram showing the configuration of a cross section of a lithium ion cell.

Here, as shown in FIG. 2, the lithium ion cell 200 is constructed for example by stacking the positive electrode 100a and the negative electrode 100b (hereinafter simply referred to as the "electrodes 100" when no distinction is made between the positive electrode 100a and the negative electrode 100b) with a separator 110 between the electrodes 100. Note that since the configuration of the lithium ion cell 200 is schematically illustrated in FIG. 2, a casing or the like that houses the electrodes 100 and the separator 110 has been omitted from the drawing.

The positive electrode 100a and the negative electrode 100b are respectively constructed by laminating a plurality of plate-like or film-like component parts that have respectively different physical properties. More specifically, as one example, as shown in FIG. 2 the positive electrode 100a includes metal foil 101a as a component part formed as a film made of aluminum and an active material layer 102a as a component part formed as a film by applying lithium cobalt oxide as an active material onto one or both surfaces (in this example, one surface) of the metal foil 101a. For such configuration, it is known that the more favorable the state of adhesion between the metal foil 101a and the active material layer 102a, the higher the performance. It is also clear from the results of research by the present inventors that the lower the interfacial resistance Rs at an interface 103a between the metal foil 101a and the active material layer 102a, the more favorable the state of adhesion (i.e., the better the adhesion).

As one example, as shown in FIG. 2, the negative electrode 100b includes metal foil 101b as a component part formed as a film made of copper (hereinafter the metal foil 101a of the positive electrode 100a described above and the metal foil 101b are collectively referred to as the "metal films 101" when no distinction is made) and an active material layer 102b as a component part formed as a film by applying carbon as an active material on one or both surfaces (in this example, one surface) of the metal foil 101b (hereinafter the active material layer 102a of the positive electrode 100a described above and the active material layer 102b are collectively referred to as the "active material layers 102" when no distinction is made). For the negative electrode 100b also, in the same way as the positive electrode 100a, it is clear from the results of research by the present inventors that the more favorable the state of adhesion between the metal foil 101b and the active material layer 102b, the higher the performance, and that the lower the interfacial resistance Rs at an interface 103b (hereinafter referred to as the "interfaces 103" when no distinction is made with the interface 103a and the interface 103a of the positive electrode 100a) between the metal foil 101b and the active material layer 102b, the more favorable the state of adhesion (i.e., the better the adhesion).

The separator 110 is a member that separates the positive electrode 100a and the negative electrode 100b to prevent short circuits, holds electrolyte inside pores, and functions so as to form channels for lithium ions between the electrodes 100. As one example, the separator 110 is a porous membrane (film) formed of a polyolefin resin such as polyethylene.

Figure 1:
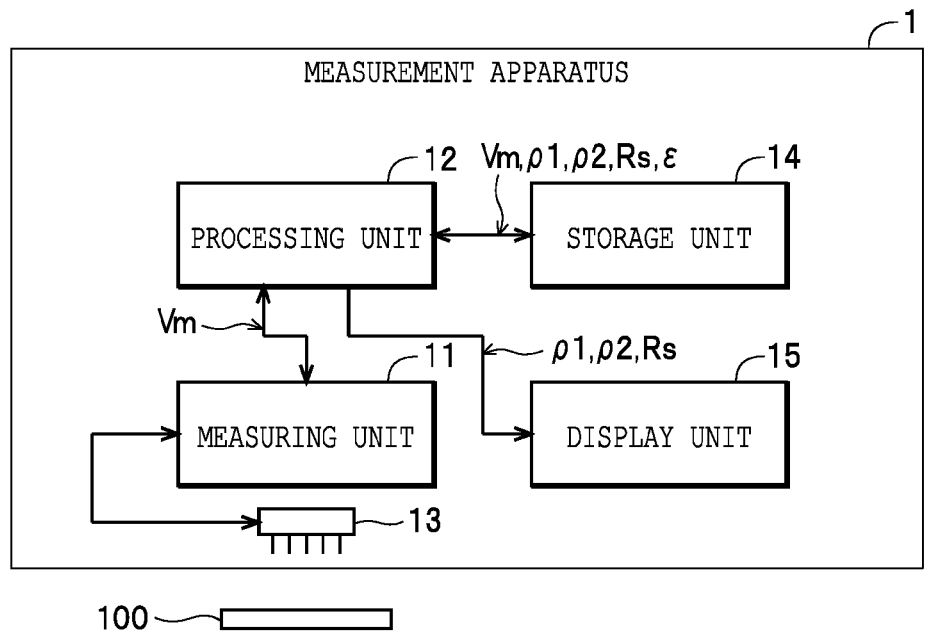
FIG. 1 is a schematic diagram showing the configuration of a measurement apparatus.

On the other hand, as shown in FIG. 1, the measurement apparatus 1 includes a measuring unit 11, a processing unit 12, a probe unit 13, a storage unit 14, and a display unit 15.

Figure 3:
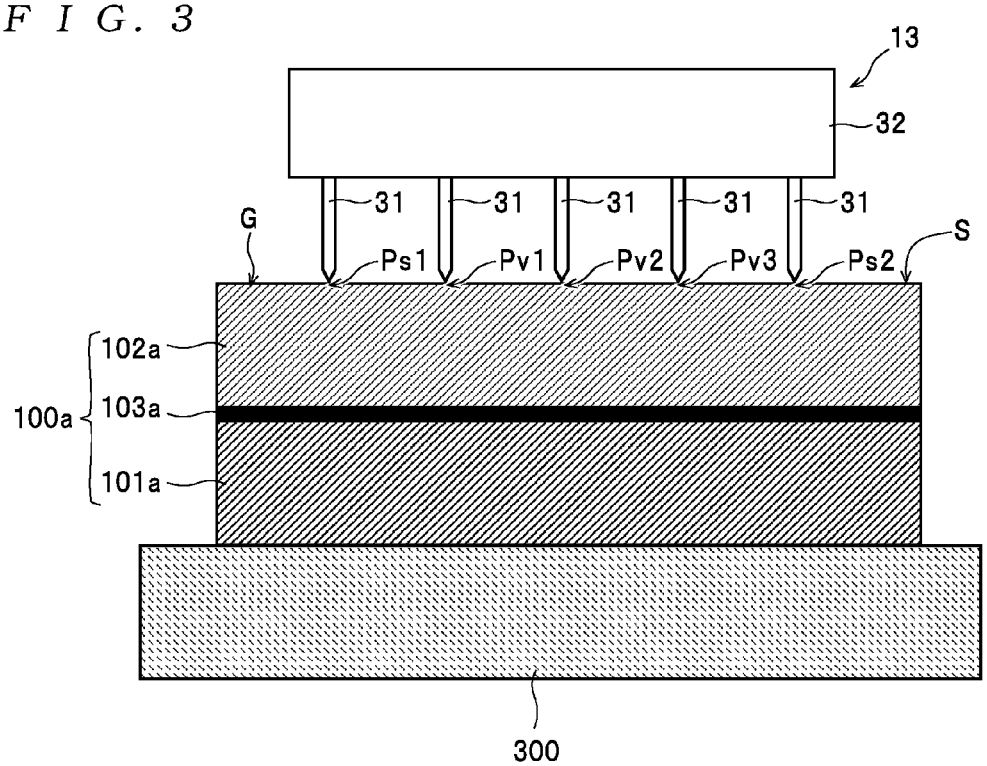
FIG. 3 is a diagram useful in explaining a method of measurement.

The measuring unit 11 includes a power supply unit and a voltage detecting unit, not shown, and carries out a potential measuring process that measures the potentials (i.e., the potential difference from the ground potential G shown in FIG. 3) of N (in this example, 3) measured positions Pv1 to Pv3 (see FIG. 3: referred to below as the "measured positions Pv" when no distinction is made) on a surface S of the electrode 100 (i.e., the active material layer 102) in a state where an electric signal (for example, a constant DC current) for measurement purposes has been supplied via the probe unit 13 to signal input positions Ps1, Ps2 (see FIG. 3) on the surface S. Here, the number N of the measured positions Pv is defined so that "N≥n" where "n" is the number of measurements of interfacial resistance or resistivity (i.e., the number of unknown values) to be made using the measurement apparatus 1. Here, in this example, three values, that is, the interfacial resistance Rs of the interface 103, the resistivity $\sigma 1$ of the metal foil 101, and the resistivity $\rho 2$ of the active material layer 102 are to be measured using the measurement apparatus 1 (i.e., n=3), and N=n (that is N=3) is defined as one example of N≥n. Note that in FIG. 3, although the surface S of the electrode 100 (the active material layer 102) is connected to ground potential G via a cable, not shown, it is possible to connect to ground potential G via a probe 31 out of the probes 31, described later, of the probe unit 13, aside from the probes 31 used to measure potential at the measured positions Pv. In such case, the position on the surface S contacted by the probe 31 for connecting to the ground potential G is not counted in the number N described above.

Figure 5:
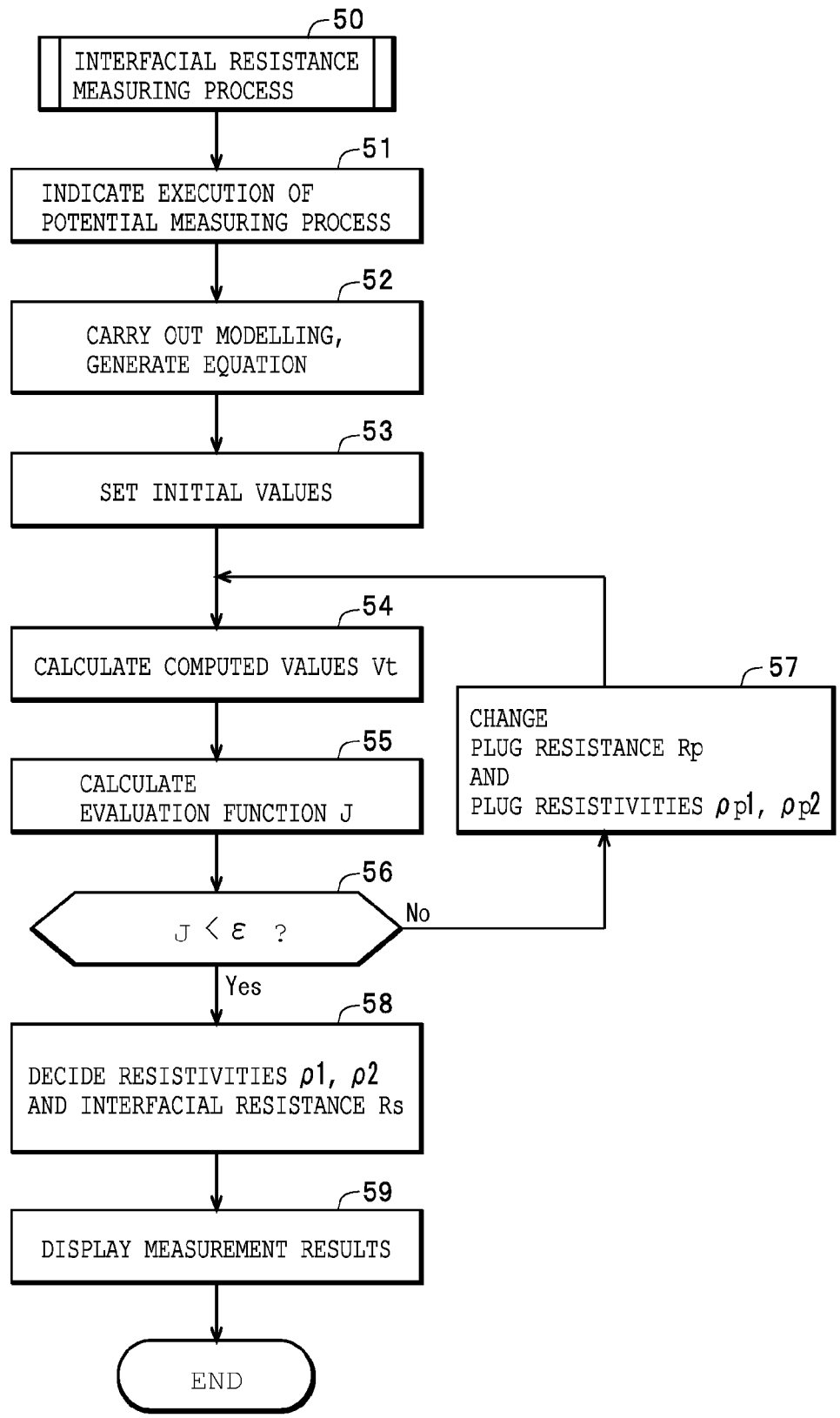
FIG. 5 is a flowchart of an interfacial resistance measuring process.

The processing unit 12 controls the measuring unit 11 to have the potential measuring process carried out. The processing unit 12 also controls the storage unit 14 to store measured values Vm that have been measured by the measuring unit 11. The processing unit 12 also carries out an interfacial resistance measuring process 50 (see FIG. 5), described later, to measure, based on the measured values Vm of the positions measured by the measuring unit 11, the interfacial resistance Rs of the interface 103 between the metal foil 101 and the active material layer 102 of the electrode 100, the resistivity $\rho 1$ of the metal foil 101, and the resistivity $\rho 2$ of the active material layer 102. The processing unit 12 also has the display unit 15 display the resistivities $\rho 1$, $\rho 2$ and the interfacial resistance Rs that have been measured.

The probe unit 13 includes the plurality of probes 31 and a support portion 32 that supports the probes 31. Here, as one example, the probe unit 13 includes a total of five probes 31 composed of two probes 31 that contact the signal input positions Ps1, Ps2 and three probes 31 that contact the measured positions Pv1 to Pv3.

The storage unit 14 stores the measured values Vm measured by the measuring unit 11 and also the resistivities $\rho 1$, $\rho 2$ and the interfacial resistance Rs measured by the processing unit 12 in accordance with control by the processing unit 12. The storage unit 14 also stores a threshold ε (a predefined value that is defined in advance) used in the interfacial resistance measuring process 50 carried out by the processing unit 12. Here, the threshold ε is a value that is compared with an evaluation function J (ρ1, Rs, ρ2), described later, calculated in the interfacial resistance measuring process 50 to determine whether the evaluation function J (ρ1, Rs, ρ2) is moving toward convergence, and the closer such threshold ε is to "0", the higher the precision being demanded for the measurement of interfacial resistance Rs. The display unit 15 displays the resistivities ρ1, ρ2, and interfacial resistance Rs that have been measured by the processing unit 12 in accordance with control by the processing unit 12.

Next, a method of using the measurement apparatus 1 to measure the resistivity ρ1 of the metal foil 101, the resistivity ρ2 of the active material layer 102, and the interfacial resistance Rs of the interface 103 between the metal foil 101 and the active material layer 102 as the component parts that construct the electrodes 100 of the lithium ion cell 200 shown in FIG. 2 will be described.

First when the positive electrode 100a is set as the measured object, as shown in FIG. 3, the positive electrode 100a is placed on a stage 300 in a state where the active material layer 102a faces upward. Next, the probe unit 13 is placed on the active material layer 102a of the positive electrode 100a in a state where the front ends of the probes 31 face downward. At this time, as shown in FIG. 3, the front ends of the probes 31 respectively contact the signal input positions Ps1 and Ps2 and the measured positions Pv1 to Pv3 on the surface S of the active material layer 102a.

After this, an operation unit, not shown, is operated to indicate the start of measurement. In accordance with this, the processing unit 12 carries out the interfacial resistance measuring process 50 shown in FIG. 5. In the interfacial resistance measuring process 50, the processing unit 12 instructs the measuring unit 11 to carry out the potential measuring process (step 51).

In the potential measuring process, the measuring unit 11 outputs an electrical signal for measurement purposes (for example, a constant DC current) from a power supply unit, not shown. At this time, the electrical signal is supplied via the probes 31 of the probe unit 13 to the signal input positions Ps1 and Ps2 on the surface S of the positive electrode 100a (the active material layer 102a). After this, the measuring unit 11 detects the potential at the measured positions Pv1 to Pv3 on the surface S (i.e., the potential differences between the ground potential G and the respective measured positions Pv for a case where the ground potential G shown in FIG. 3 is set at 0V) using the voltage detecting unit and outputs the resulting measured values Vm (i.e., data showing the measured values Vm) to the processing unit 12. After this, the processing unit 12 stores the measured values Vm in the storage unit 14.

Figure 4:
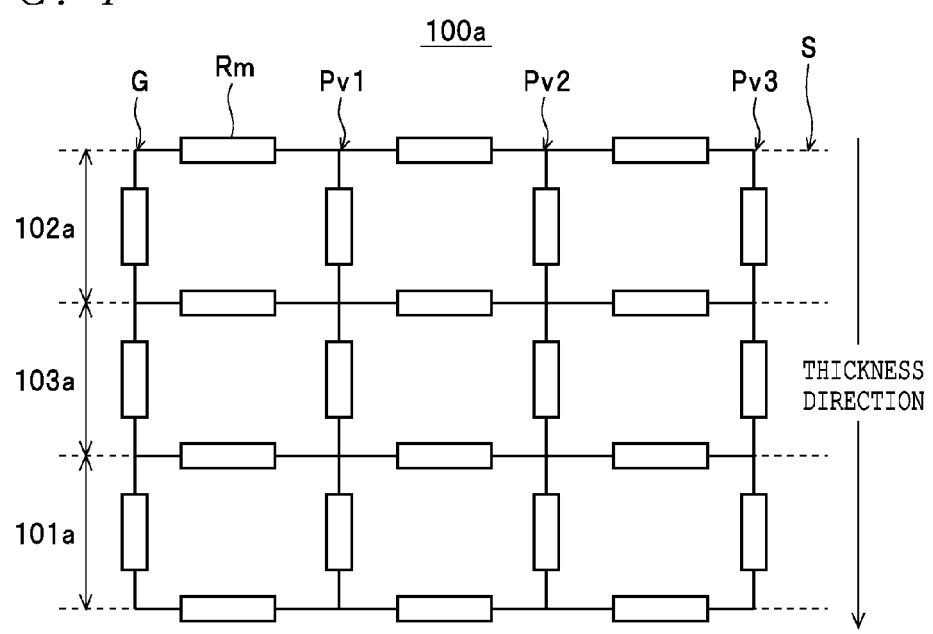
FIG. 4 is an equivalent circuit diagram showing the potentials at various positions on a positive electrode.

After this, the processing unit 12 calculates a computed value Vt of the potential at each measured position Pv on the positive electrode 100a. More specifically, as schematically shown in FIG. 4, the processing unit 12 carries out modelling in accordance with an algorithm decided in advance to construct an equivalent circuit which is composed of model resistances Rm arranged in a matrix and which shows the potentials at respective positions on the positive electrode 100a. Also, from the generated equivalent circuit, the processing unit 12 generates an equation for calculating the computed values Vt of the potentials at the measured positions Pv1 to Pv3 (such equation includes the interfacial resistance Rs and the resistivities ρ1, ρ2 as parameters (variables) and hereinafter such equation is expressed as "Vt(ρ1, Rs, ρ2)") (step 52). Note that it is possible to use a configuration where such equivalent circuit and equation are stored in advance in the storage unit 14 and the processing unit 12 generates the equation by reading out the equivalent circuit from the storage unit 14 and/or reads the equation out from the storage unit 14.

Next, the processing unit 12 sets the initial values of a plug resistivity ρp1 of the resistivity ρ1, a plug resistivity ρp2 of the resistivity ρ2, and a plug resistance Rp of the interfacial resistance Rs that are to be plugged into the equation Vt(ρ1, Rs, ρ2) described above (step 53). Here, it is possible to set the values of the plug resistance Rp and the plug resistivities ρp1, ρp2 to be set as initial values at arbitrary values. As one example, it is possible to use typical values that can be supposed from the materials of the metal foil 101a and the active material layer 102a.

Next, the processing unit 12 plugs the plug resistance Rp and the plug resistivities ρp1, ρp2 into the equation Vt(ρ1, Rs, ρ2) to calculate the computed values Vt at the respective measured positions Pv1 to Pv3 (step 54).

After this, the processing unit 12 calculates, for each measured position Pv, the difference between the measured value Vm of potential measured by the measuring unit 11 (and stored in the storage unit 14) and the computed value Vt that has been calculated. Here, the process that calculates the difference corresponds to a "comparison process" for the present invention and the calculated difference corresponds to a "comparison result" for the present invention. The processing unit 12 calculates a sum of squares for the calculated differences and also calculates an average of the calculated sum of squares (a value produced by dividing the sum of squares by the number of measured positions Pv). Here, values calculated in this way (values calculated by a least-squares method as one example of a statistical method that uses difference values) can be regarded as a function that changes according to the plug resistance Rp and the plug resistivities ρp1, ρp2, and hereinafter such function is referred to as the evaluation function J (ρ1, Rs, ρ2) or simply as the evaluation function J (step 55). Note that the relationship between the evaluation function J (ρ1, Rs, ρ2) and the sum of squares of the differences between the measured values Vm and the computed values Vt calculated for each measured position Pv is expressed by Formula (1) below.

$$J(\rho1, R2, \rho2) = \Sigma[i \in \text{Surface}]\{Vmi - Vti(\rho1, R2, \rho2)\}^2 / N \quad \text{Formula (1)}$$

Here, in Formula (1), "i" refers to numbers (in the above example, 1 to 3) assigned in order starting from one to each measured position Pv, and "Σ[i∈Surface]" refers to the addition of $\{Vmi - Vti(\rho1, R2, \rho2)\}^2$ for every measured position Pv set on the surface S of the electrode 100 (the active material layer 102). Also, as described above, "N" refers to the number of measured positions Pv set on the surface S.

After this, the processing unit 12 reads out the threshold ε from the storage unit 14, compares the calculated evaluation function J with the threshold ε and determines whether the evaluation function J is below the threshold ε (i.e., whether the comparison result satisfies a predefined condition that has bene defined in advance) (step 56). Here, when it has been determined that the evaluation function J is equal to or greater than the threshold ε (i.e., that the evaluation function J is not below the threshold ε), the processing unit 12 changes the plug resistance Rp and the plug resistivities ρp1, ρp2 (step 57) and carries out step 54 to step 56 described above. Hereafter, the processing unit 12 repeatedly carries out step 54 to step 56 when it is determined in step 56 that the evaluation function J is equal to or greater than the threshold $\epsilon$.

On the other hand, when it has been determined in step 56 that the evaluation function J is below the threshold $\epsilon$ (i.e., the comparison result satisfies the predefined condition defined in advance), the processing unit 12 decides that the plug resistivity $\rho p1$ that was plugged into the computed values $Vt(\rho1, Rs, \rho2)$ at such time is the resistivity $\rho1$, that the plug resistivity $\rho p2$ is the resistivity $\rho2$, and the plug resistance Rp is the interfacial resistance Rs (step 58). Next, the processing unit 12 has the resistivities $\rho1$, $\rho2$ and the interfacial resistance Rs that have been decided (that is, the measurement results) displayed on the display unit 15 (step 59) and ends the interfacial resistance measuring process 50. Note that step 52 to step 58 described above correspond to a "computational process which has been decided in advance" for the present invention.

After this, when the negative electrode 100b is set as the measured object, the negative electrode 100b is placed on the stage 300 in a state where the active material layer 102b faces upward. Next, in the same way as in the measurement procedure described above where the positive electrode 100a is the measured object, the probe unit 13 is placed on the negative electrode 100b and the operation unit, not shown, is then operated to indicate the start of measurement. In accordance with this, the processing unit 12 carries out the interfacial resistance measuring process 50 described above. When doing so, the processing unit 12 carries out the various processes (steps) described above to decide the resistivities $\rho1$, $\rho2$ and the interfacial resistance Rs and has the results displayed on the display unit 15.

In this way, according to the measurement apparatus 1 and the method of measurement, a potential measuring process that measures the potentials of measured positions Pv on the surface S of the electrode 100, in which the metal foil 101 and the active material layer 102 that have different physical properties are laminated, is carried out, and a computational process which has been decided in advance is carried out using the measured values Vm of potential measured by the potential measuring process to find the interfacial resistance Rs of the interface 103 between the metal foil 101 and the active material layer 102 of the electrode 100. This means that according to the measurement apparatus 1 and the method of measurement, unlike a delamination test or a cross-cut adhesion test that involve complicated tasks, it is possible to accurately and easily determine whether the state of adhesion between the metal foil 101 and the active material layer 102 is defective or non-defective based on the interfacial resistance Rs that has been measured. Also, according to the measurement apparatus 1 and the method of measurement, by measuring the resistance according to completely different measurement principles to the four-probe method that has a premise of measuring resistance of an object to be measured which is formed of a single material, it is possible to accurately measure the resistance at the interface in a laminated body in which a plurality of component parts with respectively different physical properties have been laminated. Accordingly, according to the measurement apparatus 1 and the method of measurement, it is possible to accurately and easily determine whether the state of adhesion between the metal foil 101 and the active material layer 102 of the electrode 100, which is constructed by laminating the metal foil 101 and the active material layer 102 that have different physical properties, is defective or non-defective.

Also, with the measurement apparatus 1 and the method of measurement, a comparison process that compares the computed values Vt, which have been calculated by plugging the plug resistance Rp into an equation that includes the interfacial resistance Rs as a parameter, and the measured values Vm is carried out while changing the plug resistance Rp and the plug resistance Rp when the comparison result of the comparison process satisfies a predefined condition defined in advance is set as the interfacial resistance Rs. For this reason, according to the measurement apparatus 1 and the method of measurement, it is possible to make arbitrary adjustments in accordance with the object of finding the interfacial resistance Rs, such as strictly defining the predefined condition to raise the precision of the interfacial resistance Rs or relaxing the predefined condition to reduce the processing time with priority over improvement of the precision of the interfacial resistance Rs.

Also, according to the measurement apparatus 1 and the method of measurement, the comparison process that compares the computed values Vt of potential at each measured position Pv which have been calculated by plugging the plug resistance Rp and the plug resistivities $\rho p1$, $\rho p2$ into an equation and the measured values Vm is carried out while changing the plug resistance Rp and the plug resistivities $\rho p1$, $\rho p2$, the plug resistance Rp when the comparison result of the comparison process has satisfied the predefined condition is set as the interfacial resistance Rs, and the plug resistivities $\rho p1$, $\rho p2$ when the comparison result has satisfied the predefined condition are set as the resistivities $\rho1$, $\rho2$. This means that according to the measurement apparatus 1 and the method of measurement, when the resistivity $\rho1$ of the metal foil 101 and the resistivity $\rho2$ of the active material layer 102 are unknown, it is possible to measure such resistivities $\rho1$, $\rho2$ together with the interfacial resistance Rs. Accordingly, according to the measurement apparatus 1 and the method of measurement, in addition to it being possible to accurately and easily determine whether the state of adhesion between the metal foil 101 and the active material layer 102 of the electrode 100 is defective or non-defective, it is also possible to accurately and easily determine whether the metal foil 101 and the active material layer 102 have the prescribed physical properties, for example, and as a result it is possible to make a detailed determination of whether the electrode 100 is defective or non-defective.

Also according to the measurement apparatus 1 and the method of measurement, the predefined condition is regarded as being satisfied when a value calculated by a statistical method that uses the difference between the measured values Vm and the computed values Vt is below the threshold $\epsilon$ (a defined value). This means that according to the measurement apparatus 1 and the method of measurement, when for example the number N of measured positions Pv is 2 or higher, by using least sum of squares as the statistical method, it is possible to sufficiently improve the measurement precision of the interfacial resistance Rs and the resistivities $\rho1$, $\rho2$. As a result, it is possible to accurately determine whether the state of adhesion between the metal foil 101 and the active material layer 102 of the electrode 100 is defective or non-defective and also possible to accurately determine whether the metal foil 101 and the active material layer 102 have the prescribed physical properties.

Note that the measurement apparatus, the method of measurement, and the object to be measured and not limited to the configuration, the method and the object to be measured described above. As one example, although the object to be measured in the example described above is the electrode 100 that has the metal foil 101 formed in a film as one example of a film-like or a plate-like component part, an electrode that uses a plate-like metal plate in place of the film-like metal foil 101 can be set as the object to be measured. Also, although the electrode 100 that has the active material layer 102 that has been formed as a film as one example of a film-like or a plate-like form is set as the object to be measured in the example described above, an electrode that uses a plate-like active material layer in place of the film-like active material layer 102 can be set as the object to be measured. Also, aside from the electrode 100 of the lithium ion cell 200 described above, it is possible to set various types of laminated bodies where a plurality of plate-like or film like component parts with different physical properties are laminated as the object to be measured. Also, the object to be measured is not limited to a laminated body (the electrode 100) where two component parts (i.e., the metal foil 101 and the active material layer 102) have been laminated and it is also possible to set a laminated body where three or more component parts are laminated (that is, a laminated body where two or more interfaces are present) as the object to be measured. In such case, by carrying out the interfacial resistance measuring process 50 using a formula that includes the respective interfacial resistances Rs of the two or more interfaces as parameters (variables), in the same way as the example described above, it is possible to accurately measure the interfacial resistance Rs of the respective interfaces in a laminated body in which three or more component parts with different physical properties are laminated.

Also, although an example where, as the comparison process, the differences between the measured values Vm and the computed values Vt are calculated and the plug resistance Rp when a value calculated by a least-squares method as a statistical method that uses such differences satisfies the predefined condition with respect to the threshold $\epsilon$ is set as the interfacial resistance Rs has been described above, such method is merely one example and it is possible to use other methods. As one example, it is possible to assume that the predefined condition is satisfied when the value (the evaluation function J) calculated by the least-squares method is equal to or below (i.e., not just below) the threshold $\epsilon$. It is also possible to use a method that sets the plug resistance Rp when a value that is the simple average of the differences between the measured values Vm and the computed values Vt at each measured position Pv (i.e., a value calculated by a statistical method) is below a predefined value (or is equal to or below a predefined value) is set as the interfacial resistance Rs. It is also possible to use a method that carries out a process that calculates the ratio between the measured values Vm and the computed values Vt as the comparison process and sets the plug resistance Rp when such ratio satisfies a predefined condition of being equal to or below a predefined value as the interfacial resistance Rs.

Also, although an example where the plug resistance Rp and the plug resistivities $\rho p1$, $\rho p2$ are plugged into the equation $Vt(\rho 1, Rs, \rho 2)$ that includes three parameters (variables) composed of the resistivities $\rho 1$, $\rho 2$ and the interfacial resistance Rs to measure the resistivities $\rho 1$, $\rho 2$ and the interfacial resistance Rs has been described above, it is also possible, when the resistivities $\rho 1$, $\rho 2$ are known, to treat such parameters as constants and to measure the interfacial resistance Rs by plugging the plug resistance Rp into a formula Vt(Rs) that has only the interfacial resistance Rs as a parameter. In such case, since only interfacial resistance R is to be measured using the measurement apparatus 1 (that is, the number n of unknowns is 1), the number N of measured positions Pv can also be set at 1 (that is, N=n).

Also, although the number N of measured positions Pv is set at N=n (in the example described above, N=3) for the case where the number of values of interfacial resistance and/or resistivity to be measured has been set as n, the number N of measured positions Pv can be set at an arbitrary number that is n+1 or higher (four or higher). Also, although an example where a constant DC current is used as the electrical signal for measurement purposes has been described above, when adapting the present invention to a configuration and method equipped with a current measuring unit so as to be capable of measuring current, it is possible to use a DC current in place of a constant DC current. It is also possible to adapt the present invention to a configuration and method that use an AC current (as one example, a constant AC current) in place of a DC current.

Also, although the initial values of the plug resistivity $\rho p1$, the plug resistivity $\rho p2$, and the plug resistance Rp to be plugged into the equation $Vt(\rho 1, Rs, \rho 2)$ are set at arbitrary values in the example described above, depending on such initial values, during the interfacial resistance measuring process 50 described above, the evaluation function J and the threshold $\epsilon$ may be very distant values, which would make it necessary to carry out the various processes of calculating the computed values Vt, calculating the evaluation function J, and determining whether the evaluation function J is below the threshold $\epsilon$ (i.e. steps 54 to 57 described above) repeatedly many times until the evaluation function J falls below the threshold c, which can result in a long time being required to measure the interfacial resistance Rs. In such case, by using initial values calculated by the following method (hereinafter referred to as the "initial value calculating method"), it is possible to reduce the time required to measure the interfacial resistance Rs.

Figure 6:
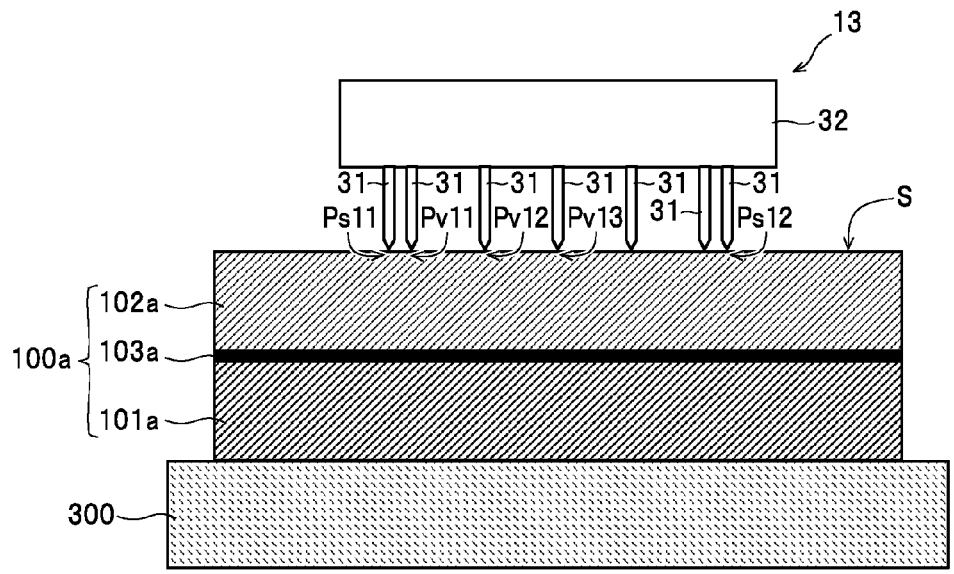
FIG. 6 is a first diagram useful in explaining an initial value calculating method.
Figure 7:
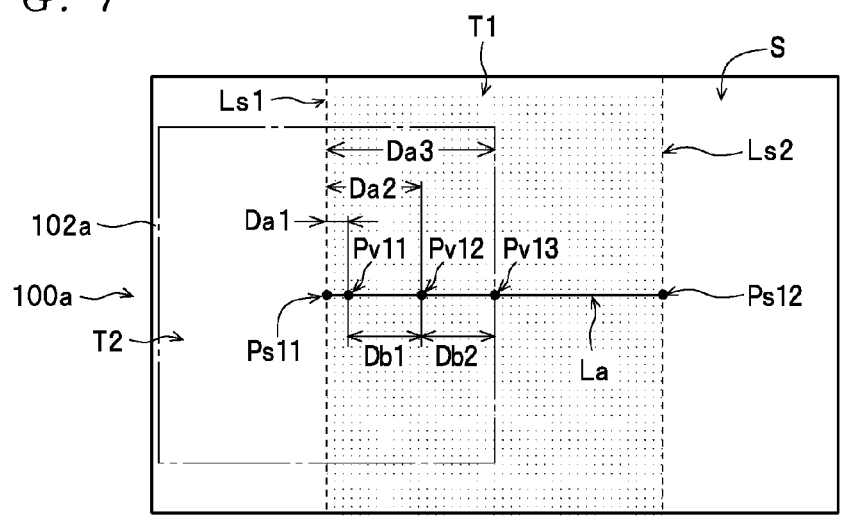
FIG. 7 is a second diagram useful in explaining the initial value calculating method.

In this initial value calculating method, as shown in FIGS. 6 and 7, signal input positions Ps11, Ps12 that supply an electrical signal for measurement purposes are set on the surface S of the active material layer 102*a* that is the component part with the higher resistivity out of the comp (i.e., the metal foil 101*a* and the active material layer 102*a*) that construct the positive electrode 100*a* as a laminated body. Also, as shown in FIG. 7, three (one example of "a plurality of") measured positions Pv11 to Pv13 (hereinafter referred to as the "measured positions Pv" when no distinction is made) are set in a partitioned area T1 on the surface S that is partitioned between two straight lines Ls1, Ls2 that respectively pass the signal input positions Ps11, Ps12 and are perpendicular to a line La that joins the signal input positions Ps11, Ps12. More specifically, the measured positions Pv11 to Pv13 are positions inside the partitioned area T1 and are set at positions where the separation distances (straight line distances) Da1 to Dai (hereinafter also referred to as the "separation distances Da" when no distinction is made) from the signal input position Ps11 (the signal input position on the source (positive electrode) side as one example of "one of the signal input positions Ps11, Ps12") respectively differ. Note that the measured position Pv11 corresponds to a "reference position" (the measured position Pv where the separation distance from the signal input position Ps11 is the shortest), the measured position Pv12 corresponds to a "first measured position", and the measured position Pv13 corresponds to a "second measured position".

Here, as shown in FIG. 7, as one example the measured positions Pv11 to Pv13 are set on the line La described above. Also, in this initial value calculating method, the measured positions Pv11 to Pv13 are set so that the intervals Db1, Db2 (hereinafter referred to as the "intervals Db" when no distinction is made) between adjacent measured positions Pv are equal.

Also, in this initial value calculating method, the measured position Pv11 is set in the vicinity of the signal input position Ps11. Also in this example, the measured position Pv13 is set at the center of the line La.

With this initial value calculating method, in the potential measuring process described above, the measuring unit 11 measures the potentials V11 to V13 at the measured positions Pv11 to Pv13 in a state where an electrical signal for measurement purposes has been supplied to the signal input positions Ps11, Ps12. The processing unit 12 also calculates the initial values of the plug resistivity ρp2 and the plug resistance Rp out of the plug resistivities ρp1, ρp2 and the plug resistance Rp based on the potentials V11 to V13 measured by the measuring unit 11.

More specifically, the processing unit 12 calculates the initial values of the plug resistivity ρp2 and the plug resistance Rp from Formulas (2) and (3) below.

$$2(R2+Rp)I = 2 \cdot M2 \quad \text{Formula (2)}$$

$$R2/Rp = \alpha(M1/M2) \quad \text{Formula (3)}$$

Figure 8:
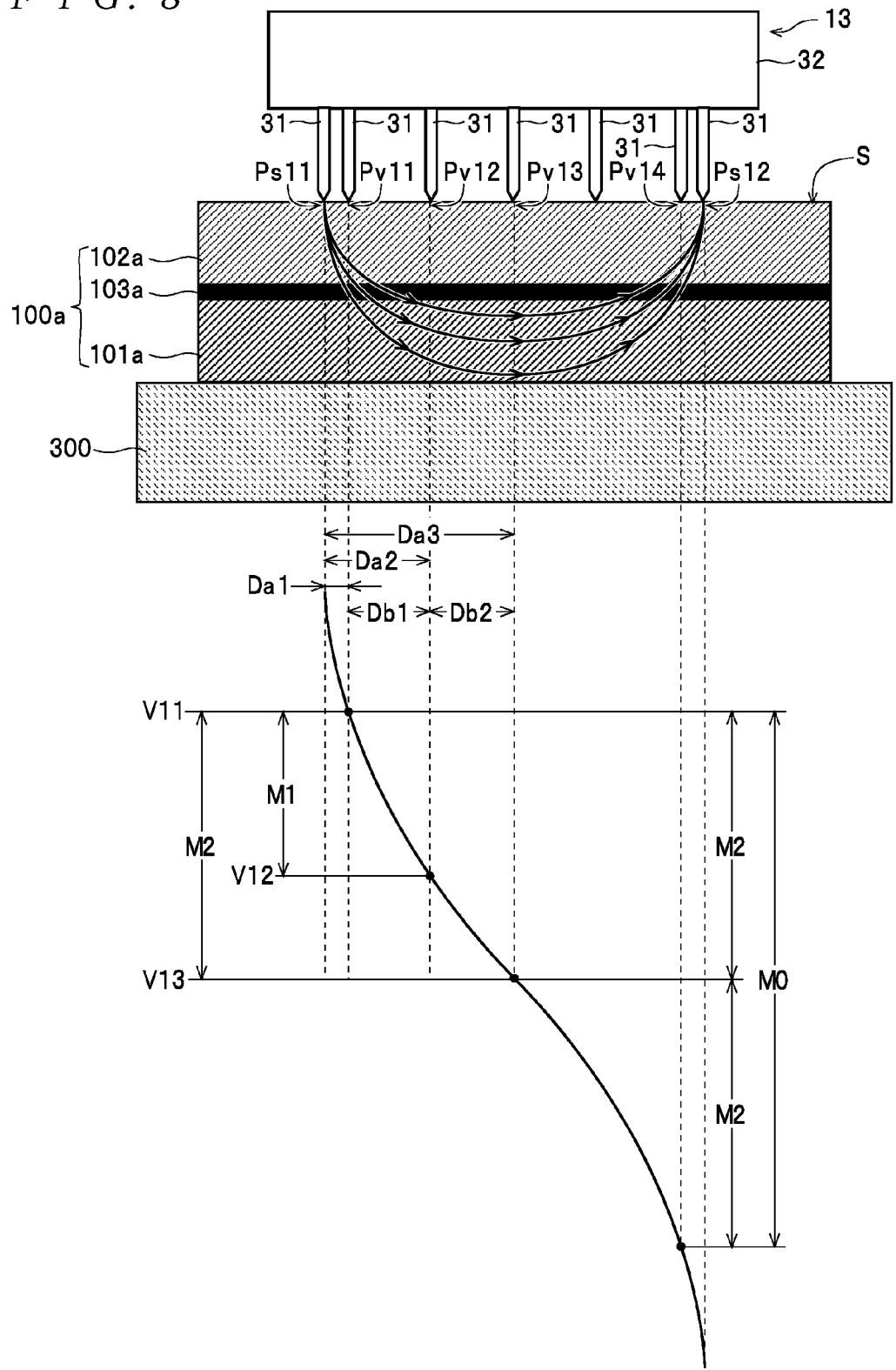
FIG. 8 is a third diagram useful in explaining the initial value calculating method.

In Formulas (2), (3), M1 expresses the difference (V11−V12) between (the measured value Vm of) the potential V11 at the measured position Pv11 as the reference position and (the measured value Vm of) the potential V12 at the measured position Pv12 (see FIG. 8) and M2 expresses the difference (V11−V13) between the potential V11 and (the measured value Vm of) the potential V13 at the measured position Pv13 (see FIG. 8). Also, "I" expresses the current of the electrical signal for measurement purposes flowing between the signal input positions Ps11, Ps12.

Also, in Formulas (2) and (3), R2 is the resistance of a predefined area T2 (see FIG. 7) that is defined in advance and is centered on the signal input position Ps11 on the active material layer 102a and is defined by Formula (4) below.

$$R2 = \rho p2(d2/S2) \quad \text{Formula (4)}$$

In Formula (4), "d2" expresses the thickness of the active material layer 102a and "S2" expresses the area of the defined area T2 described above. Here, as shown in FIG. 7, the defined area T2 is defined for example as a square area that is centered on the signal input position Ps11 and where the length of one side is length of the line La.

Also, in Formula (3), α is a coefficient for matching the order (number of digits) in the "R2/Rp" value and the order of the "M1/M2" value and can be set arbitrarily (as one example, a positive value of around 0.5 to 1).

Formulas (2) and (3) described above will now be described with reference to FIG. 8. As shown in FIG. 8, the electrical signal for measurement purposes supplied from the signal input position Ps11 passes through the active material layer 102a and the interface 103a in the vicinity of the signal input position Ps11 to flow inside the metal foil 101a, and then passes through the active material layer 102a and the interface 103a in the vicinity of the signal input position Ps12 so as to flow to the signal input position Ps12. Here, if the current of the electrical signal for measurement purposes that flows between the signal input positions Ps11, Ps12 is set as "I", the potential difference M0 between the measured position Pv11 in the vicinity of the signal input position Ps11 and the potential Pv14 (see FIG. 8) in the vicinity of the signal input position Ps12 is expressed, when the resistance of the active material layer 102a and the resistance of the interface 103a in the vicinity of the signal input position Ps12 are respectively R2 and Rp, by Formula (5) below.

$$M0 = 2(R2+Rp)I \quad \text{Equation (5)}$$

The potential difference M0 is expressed as double the potential difference M2 described above, or in other words, as shown in Formula (6) below.

$$M0 = 2 \cdot M2 \quad \text{Formula (6)}$$

Formula (2) is derived from Formulas (5) and (6) above.

On the other hand, when the interfacial resistance Rs of the interface 103a is high, for example, since it will be difficult for the electrical signal to flow from the active material layer 102a into the metal foil 101a and easy for electrical signal to flow in the active material layer 102a whose resistance is high, the potential V will gradually decrease in accordance with an increase in the separation distance Da in a state where the ratio of the change in the potential V to the change in the separation distance Da from the signal input position Ps11 does not greatly vary (i.e., the change in the potential V is small). On the other hand, when the interfacial resistance Rs of the interface 103a is low, since it will be easy for the electrical signal to flow from the active material layer 102a via the interface 103a into the metal foil 101a, in the vicinity of the signal input position Ps11 the potential V will greatly change in accordance with a change in the separation distance Da (i.e., the change in the potential V is large) and in the vicinity of the measured position Pv13, there is little change in the potential V in response to a change in the separation distance Da.

From this, it is understood that the larger the interfacial resistance Rs of the interface 103a, the smaller the ratio of the difference M1 to the difference M2 (i.e., the smaller the change in the potential V), and the smaller the interfacial resistance Rs, the larger the ratio of the difference M1 to the difference M2 (i.e., the larger the change in the potential V). Here, the larger the interfacial resistance Rs, the smaller the ratio of the resistance R2 of the active material layer 102a to the interfacial resistance Rs, and the smaller the interfacial resistance Rs, the larger the ratio of the resistance R2 of the active material layer 102a to the interfacial resistance Rs. Accordingly, it is understood that the lower the ratio (that is, R2/Rp) of the resistance R2 of the active material layer 102a to the plug resistance Rp of the interfacial resistance Rs, the lower the ratio (that is, M1/M2) of the difference M1 to the difference M2, and the larger the ratio (R2/Rp) of the resistance R2 of the active material layer 102a to the plug resistance Rp of the interfacial resistance Rs, the larger the ratio (M1/M2) of the difference M1 to the difference M2, or in other words, (R2/Rp) and (M1/M2) are in a proportional relationship, which leads to Formula (3) described above. Also, as described above, it is understood that Formula (3) described above is a relational expression that defines the relationship between the ratio ("first ratio") between the differences M1, M2 in the potentials V at the two pairs of measured positions Pv11, Pv13 and Pv11, Pv12 and the ratio (second ratio) between the resistance R2 specified from the resistivity ρ2 and the interfacial resistance Rs.

Solving for ρp2 and Rp using Formulas (2), (3), and (4) described above leads to Formulas (7) and (8).

$$\rho p2 = M2 \cdot S2/(I(1+((2 \cdot M2)/(\alpha \cdot M1)))d2) \quad (7)$$

$$Rp = M2/(I(1+(\alpha \cdot M1)/(2 \cdot M2))) \quad (8)$$

By plugging the differences M1, M2 calculated from the potentials V11 to V13 into Formulas (7), (8) described above, the respective initial values of plug resistivity ρp2 and the plug resistance Rp are calculated. Note that since the metal foil 101a is formed of aluminum, it is possible to use the known resistivity ρ1 of aluminum as the initial value of the plug resistivity ρp1.

In the interfacial resistance measuring process 50, by using the initial values of the plug resistance Rp and the plug resistivity ρp2 calculated by the initial value calculating method described above, it is possible, in the initial calculation of the evaluation function J, to produce a state where the evaluation function J and the threshold ε are quite close. This means that according to this configuration and method, compared to a configuration and method that arbitrarily define the initial values of the plug resistance Rp and the plug resistivity ρp2, it is possible to reduce the number of iterations of various processes, that is, calculation of the computed values Vt, calculation of the evaluation function J, and determination of whether the evaluation function J is below the threshold ε, until the evaluation function J falls below the threshold ε. Accordingly, according to the present configuration and method, it is possible to sufficiently reduce the time required to measure the interfacial resistance Rs.

Also, according to the present configuration and method, when measuring the interfacial resistance of the electrode 100 in which two laminated bodies are laminated, the potentials V of the three measured positions Pv11 to Pv13 where the separation distance from the signal input position Ps11 differs are measured and initial values of the plug resistance Rp and the plug resistivity ρp2 are calculated based on the relational expression that defines the relationship between first ratio and the second ratio for two pairs. This means that compared to a configuration and method that measure the potential V at three or more measured positions Pv and calculate the initial values of the plug resistance Rp and the plug resistivity ρp2 based on a relational expression that defines the relationship between the first ratio and the second ratio for three or more pairs, the calculation of the initial values is simplified, which makes it possible to further reduce the time required to measure the interfacial resistance Rs.

Also, according to the present configuration and method, the measured position Pv11 that is at the shortest separation distance from one of the signal input positions Ps11 is used as the reference position and the initial values are calculated with such reference position as one of the measured positions Pv in the two pairs. This means that according to the present configuration and method, compared to a configuration and method that calculate the respective initial values using the difference M found with adjacent measured positions Pv as the pairs, since the differences M of the respective pairs are clearly different, it is possible to set the initial values of the plug resistance Rp and the plug resistivity ρp2 calculated by plugging such differences M into the relational expression at more appropriate values.

Also, according to the present configuration and method, the measured position Pv12 at a short separation distance Da from the measured position Pv11 as the reference position and the reference position itself are set as the first pair, the measured position Pv13 at a long separation distance Da from the reference position and the reference position itself are set as the second pair, and the initial values are calculated based on a relational expression where the ratio between the difference M for the first pair to the ratio between the difference M for the second pair is set as the first ratio and the ratio of the resistance R2 of the active material layer 102 to the interfacial resistance Rs is set as the second ratio. This means that according to the present configuration and method, by defining and standardizing the measured positions Pv that compose the respective pairs in this way, it is possible, when generating the relational expression between the first ratio and the second ratio, to standardize appropriate coefficients that associate the first ratio and the second ratio, by doing so it becomes easy to generate the relational expression, and as a result it is possible to calculate the initial values of the plug resistance Rp and the plug resistivity ρp2 much more easily.

Also, according to the present configuration and method, by setting the measured positions Pv11 to Pv13 on the line La that joins the signal input positions Ps11, Ps12, a change in potential V in accordance with the separation distance Da from the signal input position Ps1 will clearly appear compared to a configuration and method where the measured positions Pv are not located on a single straight line, for example. This means that according to the present configuration and method, it is possible to set the initial values of the plug resistance Rp and the plug resistivity ρp2 calculated by plugging the differences M1, M2 found from the potentials V into the relational expression (Formula (3) described above) that defines the relationship between the first ratio and the second ratio at more appropriate values.

Also, according to the present configuration and method, the measured position Pv 13 as the second measured position is set at the center of the line La. Here, the potential V at each position on the line La will normally have the same magnitude but with opposite polarity, centered on the center of the line La. This means that according to the present configuration and method, since it is possible to define the first ratio using the difference M between the potential V of a measured position Pv set between one of the signal input positions Ps11 and the measured position Pv13 (i.e., the center of the line La), it is possible to simplify the relational expression (Formula (3) described above) that defines the relationship between the first ratio and the second ratio, and as a result it is possible to greatly simplify the calculation of the initial values of the plug resistance Rp and the plug resistivity ρp2.

Also, according to the present configuration and method, by setting the measured positions Pv so that the intervals Db between adjacent measured positions Pv are equal, compared to a configuration and method where the intervals Db between adjacent measured positions Pv are different, it is possible to simplify the relational expression (Formula (3) described above) that defines the relationship between the first ratio and the second ratio, and therefore possible to calculate the initial values of the plug resistance Rp and the plug resistivity ρp2 even more easily.

Note that although the three measured positions Pv11 to P13 are set and the first ratio is found for the differences M for two pairs in the initial value calculating method described above, it is also possible to use a configuration and method that set four or more measured positions Pv and find the first ratio for the differences M for three or more pairs.

Although an example where the measured position Pv11 where the separation distance from one of the signal input positions Ps11 is the shortest is defined as the reference position has been described above, it is also possible to use a configuration and method that set a measured position Pv aside from the measured position Pv11 as the reference position. Also, although an example where the measured position Pv12 where the separation distance Da from the reference position is short and the reference position itself are set as the first pair and the measured position Pv13 where the separation distance Da from the reference position is long and the reference position itself are set as the second pair has been described, the combinations of measured positions Pv set as the first pair and the second pair can be changed arbitrarily.

Also, although an example where the measured positions Pv are set on the line La that joins the signal input positions Ps1, Ps2 has been described, it is also possible to use a configuration and method that set the measured positions Pv on a straight line aside from the line La or a configuration and method that set the measured positions Pv at arbitrary positions inside the partitioned area T1. In addition, although an example where the measured position Pv13 is set at the center of the line La has been described above, it is also possible to use a configuration and method that set the measured position Pv13 at a position aside from the center of the line La or at a position away from the line La. In addition, although an example where the measured positions Pv are set so that the intervals Db between adjacent measured positions Pv are equal has been described above, it is also possible to use a configuration and method that set the measured positions Pv so that the intervals Db are different.

Although an example where the measured position Pv11 is set in the vicinity of the signal input position Ps11 has been described above, it is also possible to use a configuration and method that set the measured position Pv11 and the signal input position Ps11 at the same position (i.e., so that the separation distance Da between the measured position Pv11 and the signal input position Ps11 is "0"). When such configuration and method are used, it is also possible to use a configuration and method that uses a probe 31 that contacts the signal input position Ps11 and supplies an electrical signal for measurement purposes as the probe 31 for measuring the potential of the measured position Pv11 (i.e., to use a single probe for both uses).

Figure 9:
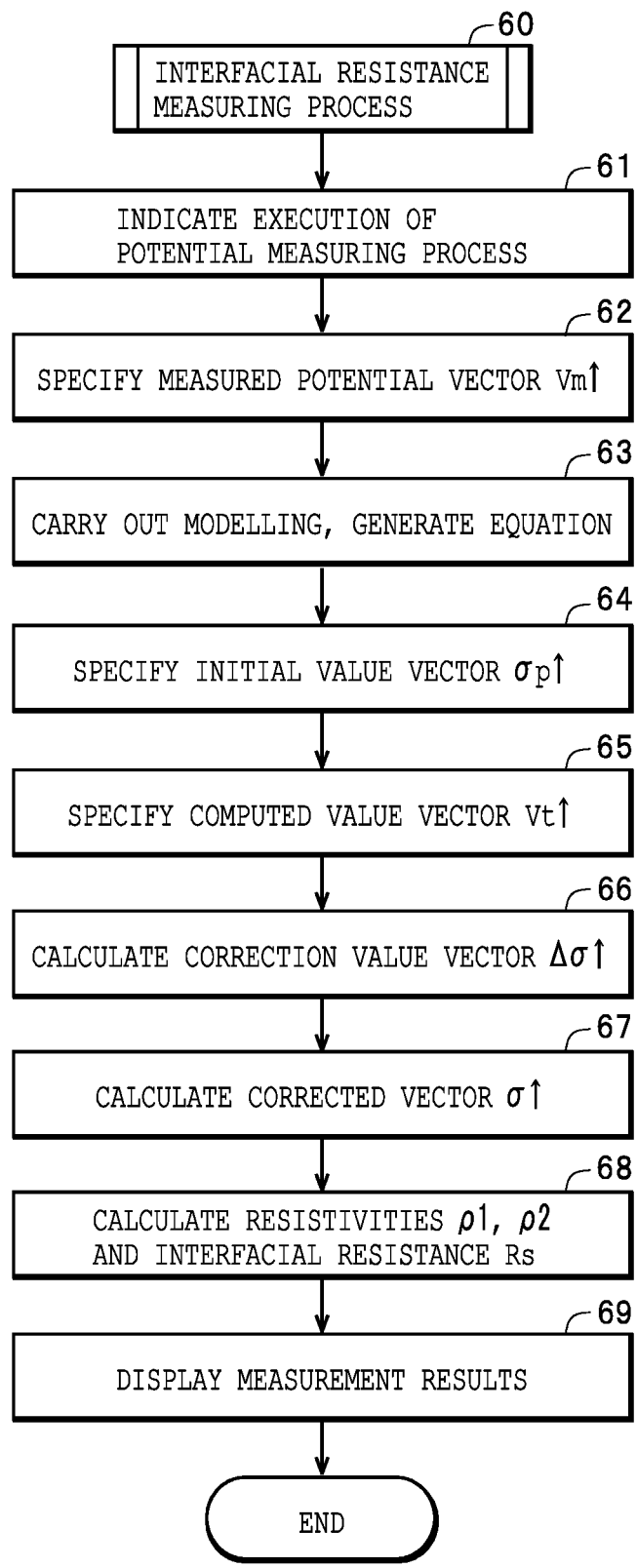
FIG. 9 is a flowchart of an interfacial resistance measuring process.

It is also possible to use a configuration and method that measure the resistivities $\rho1$, $\rho2$ and the interfacial resistance Rs based on the measured values Vm of potential measured by the measuring unit 11 by having the processing unit 12 carry out an interfacial resistance measuring process 60 shown in FIG. 9 in place of the interfacial resistance measuring process 50 described above. An example where the resistivities $\rho1$, $\rho2$ and the interfacial resistance Rs are found by carrying out such interfacial resistance measuring process 60 is described below. Note that duplicated description of the content that is the same as the interfacial resistance measuring process 50 is omitted from the following description.

In this interfacial resistance measuring process 60, the processing unit 12 instructs the measuring unit 11 to carry out a potential measuring process (step 61). In response to this, the measuring unit 11 measures the potential at the measured positions Pv1 to Pv3 (see FIG. 3) on the surface S of the electrode 100 and outputs the measured values Vm1 to Vm3 to the processing unit 12. After this, in order to treat the measured values Vm1 to Vm3 as a single group, the processing unit 12 specifies vector values based on the measured values Vm1 to Vm3 (hereinafter, such vectors values are also referred to as the "measured potential vector $Vm_\uparrow$") (step 62) and stores such measured potential vector $Vm_\uparrow$ in the storage unit 14.

Next, the processing unit 12 carries out modelling to generate an equivalent circuit (see FIG. 4) which is composed of model resistances Rm arranged in a matrix and which shows the potentials at positions on the electrode 100 and then generates an equation that calculates the computed values Vt1 to Vt3 at the measured positions Pv1 to Pv3 from the generated equivalent circuit (step 63). In such case, as such equation, the processing unit 12 generates an equation $Vt(\sigma1, Gs, \sigma2)$ that has the conductivity $\sigma1$ (the inverse of the resistivity $\rho1$, that is, $\sigma1=1/\rho1$) of the metal foil 101, the conductivity $\sigma2$ of the active material layer 102 (the inverse of the resistivity $\rho2$, that is, $\sigma2=1/\rho2$) and the interfacial conductance Gs between the metal foil 101 and the active material layer 102 (the inverse of the interfacial resistance Rs, that is, Gs=1/Rs) as parameters. Note that it is also possible to store such equivalent circuit and/or the equation $Vt(\sigma1, Gs, \sigma2)$ in advance in the storage unit 14.

Next, the processing unit 12 specifies vector values that are based on the initial conductivities $\sigma p1$, $\sigma p2$ and the initial interfacial conductance Gp where the initial values of the conductivities $\sigma1$, $\sigma2$ and the interfacial conductance Gs have been respectively set at arbitrary values (hereinafter, such vector values are also referred to as the "initial value vector $\sigma p_\uparrow$") (step 64).

Next, the processing unit 12 plugs the initial value vector $\sigma p_\uparrow$ into the equation $Vt(\sigma1, Gs, \sigma2)$ described above to calculate the computed values Vt1 to Vt3 of the potentials at the measured positions Pv1 to Pv3 of the equivalent circuit described above and specifies vector values based on the computed values Vt1 to Vt3 (hereinafter such vector values are also referred to as the "computed value vector $Vt_\uparrow$" (step 65).

After this, the processing unit 12 calculates a correction value vector $Ao_\uparrow$ for correcting the initial value vector $\sigma p_\uparrow$ based on the measured potential vector $Vm_\uparrow$, the computed value vector $Vt_\uparrow$, the initial value vector $\sigma p_\uparrow$, and an equivalent circuit equation (for example, a conductance matrix) that specifies the various physical quantities (potentials, currents, conductances, and the like) of the equivalent circuit described above (step 66).

After this, the processing unit 12 corrects the initial vector $\sigma p_\uparrow$ using the calculated correction vector $\Delta\sigma_\uparrow$ to calculate a corrected vector $\sigma_\uparrow(\sigma_{52} = \sigma p_\uparrow + \Delta\sigma_\uparrow)$ (step 67). Next, the processing unit 12 finds the conductivities $\sigma1$, $\sigma2$ and the interfacial conductance Gs that form the basis for constructing the corrected vector $\sigma_\uparrow$. After this, the processing unit 12 calculates the resistivity $\rho1$ (the inverse of the conductivity $\sigma1$, that is, $\rho1=1/\sigma1$) from the conductivity $\sigma1$ and calculates the resistivity $\rho2$ of the active material layer 102 (the inverse of the conductivity $\sigma2$, that is, $\rho2=1/\sigma2$) from the conductivity $\sigma2$. Also, the processing unit 12 calculates the interfacial resistance Rs (the inverse of the interfacial conductance Gs, that is, Rs=1/Gs) between the metal foil 101 and the active material layer 102 from the interfacial conductance Gs (step 68). Next, the processing unit 12 has the calculated resistivities $\rho1$, $\rho2$ and the interfacial resistance Rs (that is, the measurement results) displayed on the display unit 15 (step 69) and ends the interfacial resistance measuring process 60. Note that step 62 to step 68 described above corresponds to a computational process which has been decided in advance.

According to a configuration and method that carry out such interfacial resistance measuring process 60, in the same way as the measurement apparatus 1 and the method of measurement described above, it is possible, without carrying out a complicated tasks, to accurately and easily determine whether the state of adhesion between the metal foil 101 and the active material layer 102 in the electrode 100 constructed by laminating the metal foil 101 and the active material layer 102 that have different physical properties is defective or non-defective. According to such configuration and method, since it is also possible to find the interfacial resistance Rs from the corrected vector $\sigma_\uparrow$ calculated by carrying out a single iteration of a process that corrects an initial vector $\sigma p_\uparrow$ based on the initial conductivities $\sigma p1$, $\sigma p2$ and the initial interfacial conductance Gp that are set at the start, it is possible to find the interfacial resistance Rs in a short time compared to a configuration and method that find the interfacial resistance Rs by repeatedly carrying out a comparison process that compares the computed values Vt and the measured values Vm until the comparison result satisfies a predefined condition.

What is claimed is:

1. A measurement apparatus comprising:
a measurer that measures electric potential at measured positions on a surface of a laminated body in a state where an electrical signal has been supplied to the surface of the laminated body, the laminated body including a plurality of laminated layered component parts with different physical properties, and an interface component disposed between the plurality of layered component parts; and
a processor that carries out a predetermined computational process using measurement values of the measured electric potential to determine an interfacial resistance of the interface that is disposed between the plurality of layered component parts inside of the laminated body.

2. The measurement apparatus according to claim 1, wherein the processor carries out, as the computational process, a process that plugs a plug resistance as a plug value of the interfacial resistance into an equation that has the interfacial resistance as a parameter to calculate computed values of electric potential and carries out a comparison process that compares the computed values with the measured values while changing the plug resistance and sets the plug resistance as the interfacial resistance when a comparison result of the comparison process satisfies a predefined condition.

3. A measurement apparatus according to claim 2, wherein the processor plugs the plug resistance and plug resistivities as plug values for resistivities of the component parts into the equation that includes the interfacial resistance and the resistivities of the component parts as parameters to calculate the computed values,
carries out the comparison process that compares the computed values with the measured values while changing the plug resistance and the plug resistivities,
sets the plug resistance when the comparison result of the comparison process satisfies the predefined condition as the interfacial resistance, and
sets the plug resistivities when the comparison result of the comparison process satisfies the predefined condition as the resistivities.

4. The measurement apparatus according to claim 3, wherein the measurer measures, in a state where the electrical signal has been supplied to two signal input positions on a surface of a component part included in the laminated body, the electric potential at the measured positions, the measured positions including at least three positions that are inside a partitioned area on the surface of the component part that is partitioned between two straight lines that pass the signal input positions and are perpendicular to a line that joins the signal input positions, the measured positions having different separation distances from one of the signal input positions, and the processor
calculates a difference in the measured values at a pair of measured positions out of the measured positions for a plurality of different combinations in the pair of measured positions,
calculates, based on a relational expression defining a relationship between a first ratio that is a ratio between the differences for the plurality of combinations and a second ratio that is a ratio between the resistance of the composite body specified from the resistivity and the interfacial resistance, respective initial values of the plug resistance and the plug resistivity to be initially plugged into the equation in the comparison process, and
carries out the comparison process.

5. The measurement apparatus according to claim 4, wherein the measurer measures, in a state where the electrical signal has been supplied to two signal input positions on a surface of a composite body that has a high resistivity out of the composite bodies in the laminated body in which two composite bodies with respectively different resistivities have been laminated, the electric potential at the three measured positions with respectively different separation distances from the one of the signal input positions, and
the processor calculates the initial values based on the relational expression that defines the relationship between the first ratio and the second ratio for two pairs as the plurality of different combinations.

6. The measurement apparatus according to claim 5, wherein the processor sets a measured position with a shortest separation distance from the one of the signal input positions as a reference position and calculates the initial values with the reference position as one of the measured positions in the two pairs.

7. The measurement apparatus according to claim 6, wherein the processor
sets a first measured position, out of two measured positions aside from the reference position, at a short separation distance from the reference position and the reference position as a first pair,
sets a second measured position, out of the two measured positions, at a long separation distance from the reference position and the reference position as a second pair, and
calculates the initial values based on the relational expression that has a ratio of the differences for the first pair to a ratio of the differences for the second pair as the first ratio and has a ratio of the resistance of the component part to the interfacial resistance as the second ratio.

8. The measurement apparatus according to claim 2, wherein the processor carries out, as the comparison process, a process that calculates differences between the measured values and the computed values as the comparison result and determines that the predefined condition is satisfied when a value calculated by a statistical method using the differences is below a predefined value.

9. The measurement apparatus according to claim 4, wherein the measured positions are set on a line that joins the signal input positions.

10. The measurement apparatus according to claim 9, wherein the second measured position is set at a center of the line.

11. The measurement apparatus according to claim 4, wherein the measured positions are set so that intervals between adjacent measured positions are equal.

12. The measurement apparatus according to claim 1, wherein the layered component parts include a planar component part.

13. The measurement apparatus according to claim 1, wherein the layered component parts include a film component part.

14. A method of measurement comprising:
measuring electric potential at measured positions on a surface of a laminated body in a state where an electrical signal has been supplied to the surface of the laminated body, the laminated body including a plurality of laminated layered component parts with different physical properties, and an interface component disposed between the plurality of layered component parts; and
carrying out a predetermined computational process using measurement values of the measured electric potential to determine an interfacial resistance of the interface that is disposed between the plurality of layered component parts the inside of the laminated body.

15. The method of measurement according to claim 14, wherein a plug resistance as a plug value of the interfacial resistance is plugged into an equation that has the interfacial resistance as a parameter to calculate computed values of electric potential and a comparison process that compares the computed values with the measured values is carried out while changing the plug resistance, and
in the computational process, sets the plug resistance as the interfacial resistance when a comparison result of the comparison process satisfies a predefined condition.

* * * * *